United States Patent [19]

Mossman et al.

[11] Patent Number: 5,037,994

[45] Date of Patent: Aug. 6, 1991

[54] REGIOSELECTIVE NITRATION OF DIPHENYL COMPOUNDS

[75] Inventors: Allen B. Mossman, Wheaton; Weilong L. Chiang, Naperville, both of Ill.

[73] Assignee: Amoco Corporation, Chicago, Ill.

[21] Appl. No.: 477,243

[22] Filed: Feb. 8, 1990

Related U.S. Application Data

[62] Division of Ser. No. 327,043, Mar. 22, 1989.

[51] Int. Cl.$^5$ ............... C07C 49/167; C07C 49/173; C07C 49/227
[52] U.S. Cl. ........................... 564/419; 564/423; 568/931; 585/422
[58] Field of Search ............... 585/422; 568/930, 939, 568/931; 564/419, 423

[56] References Cited

U.S. PATENT DOCUMENTS

| | | | |
|---|---|---|---|
| 2,714,614 | 8/1955 | Weinmayr | 564/423 |
| 2,719,871 | 10/1955 | Hiatt | 585/422 |
| 2,823,235 | 2/1958 | Graham et al. | 564/423 |
| 3,466,330 | 9/1969 | Tanida et al. | 568/930 |
| 3,705,201 | 12/1972 | Massie | 585/422 |
| 4,005,102 | 1/1977 | Cook et al. | 568/930 |

OTHER PUBLICATIONS

Mar., *Advanced Organic Chemistry*, McGraw-Hill Book Company: New York (1968) pp. 386-388.

*Primary Examiner*—Richard L. Raymond
*Assistant Examiner*—Scott C. Rand
*Attorney, Agent, or Firm*—Reed F. Riley; William H. Magidson; Ralph C. Medhurst

[57] ABSTRACT

A regioselective nitration process for diphenyl compounds which can be carried out at about ambient temperature in which each ring of the diphenyl compound is selectively nitrated in the para position to form the corresponding di(4-nitrophenyl) compound. Such compounds as diphenyl carbonate, 2,2-diphenylpropane, 2,2-diphenylhexafluoropropane, diphenyl sulfide, diphenyl ketone, diphenyl sulfone, and the like can be converted to an isomeric mixture containing an enhanced amount of the corresponding di(4-nitrophenyl) compound, which mixture may be reduced or purified and reduced to the di(4-aminophenyl) analogues for use in the manufacture of polyamides, polyimides, and polyamide-imides.

1 Claim, No Drawings

REGIOSELECTIVE NITRATION OF DIPHENYL COMPOUNDS

This is a division of application Ser. No. 327,043, filed Mar. 22, 1989.

BACKGROUND OF THE INVENTION

This invention relates to the improved regioselective ambient temperature nitration of diphenyl compounds in the presence of nitrobenzene and, more particularly, to an ambient temperature nitration process, of diphenyl compounds in which each phenyl ring is selectively nitrated in the para position to form a di(4-nitrophenyl) compound. When the selective nitration process is combined with a novel regiopurification technique, essentially regiopure 2,2-di(4-nitrophenyl) carbonate can be made which may be decarboxylated and reduced to essentially regiopure di(4-nitrophenyl) ether. The regioselective nitration process taught here provides a convenient route to di(4-nitrophenyl) compounds generally, such as 2,2-di(4-nitrophenyl)propane and its hexafluoro analogue, compounds which can be reduced to the corresponding diamines to be used in polyamides, polyimides, and polyamide-imides.

The commercial preparation of substituted diphenyl compounds such as diphenyl ethers in which each ring is monosubstituted has become important because of the use of such materials, in particular, the diamino derivatives, in polyamides, polyimides, and polyamide-imides. Because of the multiplicity of regioisomers formable in the manufacture of such compounds and the difference in properties of materials made from the different isomers, it is of commercial importance to be able to cheaply produce highly regiopure compounds. In particular, it is important to be able to make highly regiopure 4,4'-compounds such as di(4-nitrophenyl) ether and 2,2-di(4-nitrophenyl)propane and its hexafluoro analogue since these compounds are easily reduced to their di(4-aminophenyl)analogues for use in the polymer industry to manufacture polyamides, etc.

A number of methods have been devised to synthesize highly regiopure dinitro and diamino compounds but the successful ones are carried out at low temperature or often begin with regiopure starting materials which have been made by costly and time-consuming procedures. See German Offenlegenschrift 2,549,036 (5 May 1977) which teaches a 93% selectivity in the nitration of diphenyl carbonate to di(4-nitrophenyl) carbonate at −15° C. to −20° C. It would be of interest therefore to find a method for making higher purity di(4-nitrophenyl) compounds directly by improving the regioselectivity of the nitrating process.

Now it has been found that by carrying out the nitration process of diphenyl compounds in the presence of nitrobenzene, not only can the regioselectivity to the para isomer be increased, but the nitration can also be effected with the improved regioselectivity at essentially ambient temperature instead of the more usual near-ice temperatures used in earlier nitrations.

BRIEF DESCRIPTION OF THE INVENTION

The invention described herein is an enhanced regioselective nitration process to nitrate each ring of a compound of formula

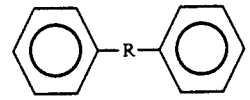

primarily in the para position, wherein R is selected from the group consisting of $-OCO_2-$, $>C(CH_3)_2$, $>C(CF_3)_2$, $>CO$, $>SO_2$, $>O$, $>CH_2$, $>CHR'$, and $>CR'R''$, and wherein $R'$ and $R''$ are $C_1$ to $C_5$ alkyl radicals, to form primarily the di(4-nitrophenyl) derivative, a process which comprises treating said compound in the presence of nitrobenzene at a temperature above about 15° C. with a nitrating agent. The invention includes also the use of the enhanced nitration process to nitrate 2,2-diphenylpropane which can be made from alpha-chlorocumene and benzene, and the subsequent reduction of the nitrated product to form an isomeric mixture containing mainly the 2,2-di(4-aminophenyl)propane isomer.

DETAILED DESCRIPTION OF THE INVENTION

The diphenyl compounds useful in this invention are of formula

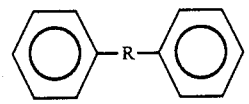

wherein R is selected from the group consisting of $-OCO_2-$, $>C(CH_3)_2$, $>C(CF_3)_2$, $>CO$, $>SO_2$ $>O$, $>CH_2$ $>CHR'$, and $>CR'R''$, and wherein $R'$ and $R''$ are $C_1$ to $C_5$ alkyl radicals. Preferred are diphenyl compounds wherein R is selected from the group consisting of $-OCO_2-$, $>C(CH_3)_2$, $>C(CF_3)_2$, $>CO$, and $>SO_2$. Most preferred are diphenyl compounds wherein R is selected from the group consisting of $-OCO_2-$, $>C(CH_3)_2$, and $>C(CF_3)_2$.

The nitration process is carried out in solution with concentrated nitric acid or a concentrated nitric acid-producing substance in conjunction with a material such as concentrated sulfuric acid or trifluorosulfonic acid. A mixture of concentrated nitric acid and sulfuric acid is preferred. However, other conventional nitrating agents can be used, too, as may be understood by one skilled in the art.

The nitration is accomplished in the presence of nitrobenzene as a nitration solvent. In general, the amount of nitrobenzene used should be in large excess and keep the diphenyl compound at least mainly in solution. The ratio of substance to be nitrated to nitrating agent should be between about 0.1 and about 0.6. The ratio does not appear critical except enough should be used to complete the reaction. The nitration is carried out preferably at above about 10° C., more preferably above about 15° C. and, most preferably, above about 17° C. Generally, nitration above a temperature of 30° C. leads to poorer yield and so a preferred upper temperature limit on the nitration process is about 25° C. and, more preferably about 20° C.

When the diphenyl compound starting material is diphenyl carbonate the nitration process of this invention can be combined with the isomeric purification technique described in U.S. Ser. No. 292,403, filed Dec. 30, 1988, entitled "Changing The Regiopurity of Mixtures Containing 4,4'-disubstituted Diphenyl Carbonates," which is incorporated by reference herein.

In this technique the crude di-(4-nitrophenyl) carbonate is mixed with p-nitrophenol and the displaced ortho- and meta-nitrophenols removed by displacement and the carbonate optionally decarboxylated. In this process the p-nitrophenol replaced the aromatic rings which are 2- or 3-nitrosubstituted and can result in essentially 100% regiopure di-(4-nitrophenyl) carbonate or ether.

The following Examples will serve to illustrates certain specific embodiments of the herein disclosed invention. These Examples should not, however, be construed as limiting the scope of the novel invention contained herein as there are many variations which may be made thereon without departing from the spirit of the disclosed invention, as those of skill in the art will recognize.

EXAMPLES

Example 1

Nitration of diphenyl carbonate in the presence of nitrobenzene.

A 2000 ml reactor equipped with a mechanical stirrer, thermometer, and a jacketed addition funnel was charged with 107.11 g of diphenyl carbonate (0.5 mol) and 500 ml of nitrobenzene. The mixture was stirred until dissolution was complete. In the meantime, the mixed acid reagent was prepared by mixing 99.02 g of concentrated nitric acid and 125 ml of concentrated sulfuric acid in a beaker with cooling. The cooled mixed-acid reagent was then poured into the jacketed addition funnel and further cooled with ice. After the diphenyl carbonate had dissolved in the reaction vessel, the temperature was adjusted to 20° C. with an ice/water bath. The mixed-acid reagent was added at a rate which maintained the temperature of the reaction mixture at close to 20° C. The total addition took around 60 min. Following the addition, the reaction was stirred for an additional 60 min. The reaction mixture was then poured over 600 ml of ice/water. A 600 ml portion of ethyl acetate was added and the mixture transferred to a separatory funnel and shaken. The organic layer was removed and the aqueous layer was washed 3 times with 100 ml portions of ethyl acetate. The organic layers were combined and washed with 200 ml of saturated sodium bicarbonate and 200 ml of saturated brine. The organic layer was then dried over sodium sulfate.

After the reaction mixture was dried, the ethyl acetate was removed by rotatory evaporation. The nitrobenzene solution of crude product was poured into 2000 ml of cyclohexane and the precipitated crude product (215.16 g) recovered by filtration. Gas chromatography showed the isomeric carbonates to be present in 95.6%, 4,4'-, 0.6%, 4,3'-, and 3.8%, 4,2'-dinitrodiphenyl carbonate, amounts. Recrystallization from a mixture of toluene and cyclohexane resulted in 142.7 g of di(4-nitrophenyl)carbonate or a 94% yield.

Comparative Example 2

Nitration of diphenyl carbonate in the absence of nitrobenzene.

A 1 l reactor equipped with a mechanical stirrer, an addition funnel, a thermometer, a condenser and a nitrogen inlet tube was charged with 10.71 g of diphenyl carbonate (0.05 mol) and 200 ml of methylene chloride. This was stirred under a slow nitrogen purge until dissolution was complete. A 50 g portion of trifluoromethanesulfonic acid (0.33 mol) was added dropwise to the reaction mixture. A 7.7 g portion of concentrated nitric acid (0.11 mol) was added dropwise at a rate which maintained the temperature at 25°±1° C. Cooling with an ice bath was used to maintain the temperature. The addition of nitric acid required 15 min. Following the addition of the acid, the ice bath was removed and the reaction mixture was stirred for 1 hr at room temperature. After 1hr the reaction was quenched by the addition of ice and the solution transferred to a separatory funnel and an additional 1 l of methylene chloride added. The aqueous and organic layers were separated and the organic layer washed with two 500 ml portions of water and sodium bicarbonate solution. The product solution was dried over sodium sulfate and concentrated to produce 16 g of crude product containing the 4,4'- and 4,2'-dinitrodiphenyl carbonates in a 77 to 23 ratio.

Comparative Example 3

Nitration of 2,2-diphenylpropane in the absence of nitrobenzene.

A 0.98 g quantity of 2,2-diphenylpropane in 10 ml of concentrated $H_2SO_4$. The mixture was cooled to 17° C. and 0.99 g of concentrated $HNO_3$ added dropwise such that the temperature was held between 17° C. and 20° C. Mechanical stirring was continued for 20 min after which the reaction mixture was added to ice. The product was extracted with methylene chloride which was evaporated to give 1.2 g (86%) of crude product. Selectivity to the 4,4'-disubstituted diphenyl product was 64%.

Example 4

A quantity of 2,2-diphenylpropane was made as follows:

Into a 3 l, three-necked, round-bottomed flask were added 1562 (20.0 mols) of dry benzene and 66.67 g (0.5 mols) of aluminum chloride. The benzene solution was stirred with a mechanical stirrer under nitrogen atmosphere in an ice-water bath.

Into this benzene solution, alpha-chlorocumene made by HCl addition to alpha-methylstyrene was added slowly over a period of 2 hr through the jacketed dropping funnel with dry-ice and acetone cooling jacket. After the completion of the addition of alpha-chlorocumene, the ice-water bath and the addition funnel were removed. The reaction mixture was stirred for another 30 min while the temperature was allowed to slowly warm up to ambient temperature.

The orange-colored reaction mixture was then poured into 2 l of ice-water and stirred for 30 min. The organic layer was separated from the aqueous layer by a separatory funnel, and dried over anhydrous magnesium sulfate. The benzene solution was filtered. The volume of the solution was reduced on a rotary evaporator. The resulting residue was then vacuum-distilled to give 335.2 g (1.71 mols) of 2,2-diphenylpropane. The yield was 85.4 mol percent.

Example 5

A quantity of 2,2-di(4-nitrophenyl)propane was made as follows:

A 1 l glass reactor equipped with baffles, mechanical stirrer, thermometer, and a jacketed addition funnel was charged with 9.80 g (0.05 mols) of 2,2-diphenylpropane, 100 ml of nitrobenzene, and 12.5 ml of sulfuric acid. The mixture was stirred and cooled in an ice bath. Meanwhile 7.70 g of 90% nitric acid (1.1 mol) and 12.5 ml of sulfuric acid were mixed in a beaker and cooled in an ice bath. The mixed acid was then transferred to the jacketed addition funnel and maintained cold with an ice bath. The temperature of the reaction mixture was adjusted to 17° C. and the mixed acid reagent was added to the well stirred reaction mixture at a rate which maintained the temperature at 17° C. With sufficient cooling the addition requires 0.25 hr. AFter the addition of the mixed acid reagent was complete, the reaction mixture was allowed to warm to room temperature and was maintained with stirring at room temperature for 1 hr. The reaction mixture was poured onto 300 g of ice. Sufficient methylene chloride was added to completely dissolve any solids present and the aqueous and organic layers were separated. The aqueous layer was extracted with 4 portions (40 ml each) of methylene chloride. The combined organic layers were washed with 100 ml of saturated sodium bicarbonate solution and 100 ml of saturated sodium chloride solution. The resulting wash organic layer was dried over anhydrous sodium sulfate.

A small portion of this solution of the crude product was analyzed by GLC. This analysis indicated a quantitative conversion of the starting material with a selectivity of 82% to the desired material. The dry organic layer was filtered to remove the hydrated sodium sulfate, and solvent was removed to in vacuo, resulting in 15.19 g of a yellow solid.

The crude product was recrystallized from 250 ml of ethanol resulting in 9.62 g (67.3%) yield of cream-colored crystals (mp 132°-134° C.).

Example 6

A quantity of 2,2-di(4-aminophenyl)propane was prepared as follows:

A 50 ml pressure vessel was charged with 5.0 g of 2,2-di(4-nitrophenyl)propane (0.0175 mol), 10 ml of methanol, and 1 g of a 1% Pd on carbon catalyst. The vessel was assembled and sequentially purged with nitrogen and hydrogen. The reactor was pressurized to 400 psig hydrogen and then stirred at 2000 rpm. The reaction spontaneously heated to 77° C., and was maintained at around 100° C. for 1 hr. The reaction was cooled to room temperature and removed from the reactor. The catalyst was removed by filtration and the solvent removed in vacuo resulting in 3.82 g (96.6%) of crude 2,2-di(4-aminophenyl)propane (mp 123°-125° C.). Analysis by GLC indicated the purity of the material was on the order of 97%.

What is claimed is:

1. A process to produce 2,2-di(4-aminophenyl)propane comprising:
   making 2,2-diphenylpropane by reacting alpha-chlorocumene with benzene in the liquid phase;
   nitrating said 2,2-diphenylpropane in the presence of nitrobenzene at a temperature above about 15° C. to produce a mixture containing predominantly the 2,2-di(4-nitrophenyl)propane isomer;
   reducing said mixture with hydrogen to obtain a mixture predominantly containing 2,2-di(4-aminophenyl)propane.

* * * * *